United States Patent [19]
Busetti et al.

[11] Patent Number: 5,788,987
[45] Date of Patent: Aug. 4, 1998

[54] METHODS FOR TREATING EARLY MORNING PATHOLOGIES

[75] Inventors: Cesare Busetti; Tiziano Crimella, both of Milan, Italy

[73] Assignee: Poli Industria Chimica SpA, Milan, Italy

[21] Appl. No.: 790,514

[22] Filed: Jan. 29, 1997

[51] Int. Cl.⁶ ............................................. A61K 9/54
[52] U.S. Cl. .................... 424/480; 424/458; 424/482
[58] Field of Search .................................. 424/480, 400, 424/458, 482; 514/313, 453, 468, 510

[56] References Cited

U.S. PATENT DOCUMENTS

| | | | |
|---|---|---|---|
| 3,131,123 | 4/1964 | Masquelier | 167/57 |
| 4,248,858 | 2/1981 | Guley et al. | 424/21 |
| 4,432,966 | 2/1984 | Zeitoun et al. | 424/21 |
| 4,713,248 | 12/1987 | Kjørnes et al. | 424/468 |
| 4,780,318 | 10/1988 | Appelgren et al. | 424/469 |
| 4,786,505 | 11/1988 | Lovgren al. | 424/468 |
| 4,786,506 | 11/1988 | Fontanelli | 424/470 |
| 4,844,905 | 7/1989 | Ichikawa et al. | 424/451 |
| 4,851,231 | 7/1989 | Urquhart et al. | 424/469 |
| 4,853,230 | 8/1989 | Lovgren et al. | 424/466 |
| 4,853,249 | 8/1989 | Takashima et al. | 427/3 |
| 4,857,337 | 8/1989 | Miller et al. | 424/480 |
| 4,863,742 | 9/1989 | Panoz et al. | 424/473 |
| 4,871,549 | 10/1989 | Ueda et al. | 424/494 |
| 4,882,169 | 11/1989 | Ventouras | 424/493 |
| 4,886,669 | 12/1989 | Ventouras | 424/469 |
| 4,888,179 | 12/1989 | Appelgren et al. | 424/480 |
| 4,910,021 | 3/1990 | Davis et al. | 424/456 |
| 4,971,805 | 11/1990 | Kitanishi et al. | 424/494 |
| 4,975,284 | 12/1990 | Stead et al. | 424/497 |
| 5,007,790 | 4/1991 | Shell | 424/451 |
| 5,035,899 | 7/1991 | Saeki et al. | 424/480 |
| 5,096,717 | 3/1992 | Wirth et al. | 424/490 |
| 5,175,003 | 12/1992 | Goldman | 424/484 |
| 5,202,338 | 4/1993 | Bar et al. | 514/314 |
| 5,217,720 | 6/1993 | Sekigawa et al. | 424/480 |
| 5,217,997 | 6/1993 | Levere et al. | 514/565 |
| 5,232,706 | 8/1993 | Palomo Coll | 424/475 |
| 5,234,947 | 8/1993 | Cherksey | 514/449 |
| 5,238,686 | 8/1993 | Eichel et al. | 424/461 |
| 5,262,172 | 11/1993 | Sipos | 424/490 |
| 5,275,824 | 1/1994 | Carli et al. | 424/490 |
| 5,294,448 | 3/1994 | Ring et al. | 424/497 |
| 5,296,233 | 3/1994 | Batista et al. | 424/463 |
| 5,302,400 | 4/1994 | Sipos | 424/494 |
| 5,316,772 | 5/1994 | Jurgens, Jr. et al. | 424/472 |
| 5,378,474 | 1/1995 | Morella et al. | 424/469 |
| 5,395,626 | 3/1995 | Kotwal et al. | 424/472 |
| 5,445,829 | 8/1995 | Paradissis et al. | 424/480 |
| 5,464,633 | 11/1995 | Conte et al. | 424/480 |
| 5,468,746 | 11/1995 | Casagrane et al. | 514/235.5 |
| 5,482,718 | 1/1996 | Shah et al. | 424/480 |
| 5,536,507 | 7/1996 | Abramowitz et al. | 424/479 |
| 5,650,156 | 7/1997 | Grinstaff et al. | 424/400 |

FOREIGN PATENT DOCUMENTS

| | | |
|---|---|---|
| 0 305 918 A1 | 3/1989 | European Pat. Off. . |
| 0 366 621 A1 | 5/1990 | European Pat. Off. . |
| 0 453 001 A1 | 10/1991 | European Pat. Off. . |
| 0 572 942 A2 | 12/1993 | European Pat. Off. . |
| 0 629 398 A1 | 12/1994 | European Pat. Off. . |

OTHER PUBLICATIONS

K. Nishimura et al.; Dosage Form Design for Improvement of Bioavailability of Levodopa VI: Formulation of Effervescent Enteric–Coated Tablets. *J. Pharm. Sci.* 73(7):942–946 (1984).

A. Gazzaniga et al.; time–dependent oral delivery systems for colon targeting. *S.T.P. Pharma Sciences* 5(1):83–88 (1995).

*Primary Examiner*—Thurman K. Page
*Assistant Examiner*—Kathryne E. Shelborne
*Attorney, Agent, or Firm*—Townsend and Townsend and Crew LLP

[57] ABSTRACT

The present invention provides methods of treating early morning pathologies using a time-specific controlled release dosage formulation which is administered prior to sleep, and which permits or achieves delivery of a pharmaceutically active agent effective for the treatment of the specific early morning pathology to be treated, at about the time of awakening. The time-specific controlled release dosage formulation comprises (1) a core including the pharmaceutically active agent(s) effective for the treatment of the early morning pathology, and (2) a swellable polymeric coating layer substantially surrounding the core. The swellable polymeric coating layer delays the release of the pharmaceutically active agent from the core for a predetermined period of time dependent upon the thickness of the swellable polymeric coating layer, to effect delivery of the pharmaceutically active agent at about the time of awakening.

27 Claims, No Drawings

5,788,987

METHODS FOR TREATING EARLY MORNING PATHOLOGIES

FIELD OF THE INVENTION

The present invention relates to methods for medical treatment. More particularly, the present invention relates to methods for treating conditions or pathologies, the symptoms of which are more pronounced in early morning.

BACKGROUND OF THE INVENTION

It is increasingly recognized that several chronic diseases display rhythmic patterns in the manifestation of symptoms. In this field there is particular interest in those conditions for which symptoms are generally aggravated in the morning. These early morning pathologies are typically treated by either night-time administration of conventional medicines or relatively constant administration of therapeutic agents with the goal of maintaining constant levels of drug in the system of the afflicted subject. By this protocol, the therapeutic benefit of the drag is assured at the time of awakening when the symptoms are generally more pronounced. Unfortunately, the low compliance of patients or the continual exposure of the system to therapeutic agents may be undesirable in some subjects or some situations. In an ideal clinical situation, drug treatment would result in highest peak plasma concentrations around the time of most frequent occurrence of symptoms. In this instance the ideal drug delivery system should allow administration at bedtime and delay the release of the drug for as many hours as is required to reach therapeutic blood levels at the more appropriate time.

Accordingly, it is an object of the present invention to provide methods of treating early morning pathologies which provide therapeutic benefits to the subject suffering therefrom while avoiding unnecessary exposure of the body to the therapeutic agent. It is a further object of the present invention to provide a pharmaceutical formulation for the time-specific delivery of a pharmaceutically active agent for the treatment of early morning pathologies.

SUMMARY OF THE INVENTION

As a first aspect, the present invention provides a method for treating an early morning pathology. As used herein, the phrase "early morning pathology" relates to a pathologies, conditions, disorders, diseases, or other illnesses the symptoms of which are typically more pronounced, aggravated or acute during the last hours of sleeping-time or after the afflicted subject awakens from sleep. Most humans sleep at night, however, some humans have alternate sleep schedules. Therefore, the term "early morning" relates to the state of awakening from sleep as opposed to the time of day. Individuals whose sleep schedule involves sleeping during the daytime and working at night may exhibit some of these pathologies in the evening or night when they awaken from sleep.

The methods of the present invention comprise administering to a subject in need of treatment, a time-specific controlled release dosage formulation which is administered prior to sleep, and which permits or achieves delivery of a pharmaceutically active agent effective for the treatment of the specific morning pathology to be treated, at about the time of awakening or a few hours in advance of awakening. The time-specific controlled release dosage formulation comprises (1) a core including the pharmaceutically active agent(s) effective for the treatment of the early morning pathology, and (2) a swellable polymeric coating layer substantially surrounding the core. The swellable polymeric coating layer delays the release of the pharmaceutically active agent from the core for a predetermined period of time dependent upon the thickness of the swellable polymeric coating layer, to effect delivery of the pharmaceutically active agent at the more appropriate time (e.g., at about the time of awakening).

As a second aspect, the present invention provides a pharmaceutical formulation for the time-specific delivery of a pharmaceutically active agent to a subject in need of the therapeutic effects thereof. The formulation comprises: (1) a core comprising the pharmaceutically active agent and a disintegration enhancing agent; and (2) a swellable polymeric coating layer substantially surrounding the core. The swellable polymeric coating layer delays the release of said pharmaceutically active agent from the core for a predetermined period of time dependent upon the thickness of said swellable polymeric coating layer. The disintegration enhancing agent accelerates the disintegration of the core upon disintegration of the swellable polymeric coating layer to improve the rate of release of the pharmaceutically active agent from the core when the desired time for release is reached.

As a third aspect, the present invention provides a pharmaceutical formulation for the time-specific delivery of a pharmaceutically active agent to a subject in need thereof. The formulation comprises: (1) a first time-specific dosage unit comprising (a) a core containing the pharmaceutically active agent and a disintegration enhancing agent; and (b) a swellable polymeric coating layer substantially surrounding the core; and (2) a second time-specific dosage unit comprising (a) a core containing the pharmaceutically active agent; and (b) a swellable polymeric coating layer substantially surrounding the core. The swellable polymeric coating layer delays the release of the pharmaceutically active agent from the core for a predetermined period of time dependent upon the thickness of the swellable polymeric coating layer. The disintegration enhancing agent accelerates the disintegration of the core upon dissolution of the swellable polymeric coating layer to improve the rate of release of the pharmaceutically active agent from the core. In this embodiment, the core containing the active ingredient may be differently formulated so as to allow the prompt release of the active component or a further controlled or sustained release, after the desired lag-time. For this purpose, either conventional core excipients or excipients which are capable of forming a matrix system may be used.

These and other objects and aspects of the present invention are set forth in further detail in the detailed description and examples hereinbelow.

DETAILED DESCRIPTION OF THE INVENTION

The present invention provides methods of treating morning pathologies. Examples of specific late night-time or early morning pathologies include but are not limited to, asthma, angina, hypertension, myocardial or cerebral infarction, arthritis, incontinence, Parkinson's disease or Parkinsonism and sleep disorders (e.g. those related to anticipated wakening). In each of these conditions, the symptoms of the condition are typically aggravated, more acute, or worse during the night, or just after the subject awakens. The term "sleep" as used herein refers to a prolonged period of rest during which the individual exhibits decreased activity. Typically sleep is a period of rest lasting for 3 or more hours, more typically about 6–8 hours for most adult humans. The term "sleep" as used herein relates to periods of resting wherein all the clinical stages of sleep are not achieved as well as periods of rest wherein all the clinical stages of sleep are achieved. The term "awaken" or "awakening" relates to the physical condition of arousal from sleeping or resting, and is characterized by an increase in the level of physical activity. The period of awakening is generally understood to occur from about 4 or more hours after the commencement of sleep.

The methods and pharmaceutical formulations of the present invention are useful for the treatment of the foregoing late night-time or early morning pathologies in that the methods and formulations of the present invention are useful for effecting the delivery of a pharmaceutically active agent at about late night-time or early morning, at which time the symptoms of early morning pathologies are typically aggravated or more acute. The specific pharmaceutically active agents employed in the methods and formulations of the present invention will of course, depend upon the specific morning pathology which is desireously treated. The pharmaceutically active agent delivered according the methods of the present invention or using the formulations of the present invention is a pharmaceutically active agent which is therapeutically effective against the condition or pathology being treated.

Examples of specific pharmaceutically active agents which may be included in the pharmaceutical formulations of the present invention include but are not limited to antiasthmatics, antiangina agents, antiarthritis agents, antiarrhythmic and antihypertensive agents, anticoagulant and antiplatelet agents, anti-Parkinson agents, sedatives, ansiolytic agents, anticholinergic and antispasmodic agents, vasopressin analogues, and peptide and biopolymeric agents.

In the embodiment wherein the early morning pathology which is desireously treated is asthma, the pharmaceutically active agent of the formulation is an antiasthmatic agent. Specific examples of antiasthmatic agents include but are not limited to steroids, such as betamethasone, dexamethasone, methylprednisolone, prednisolone, prednisone, triamcinolone and the like; xanthines such as theophylline, aminophylline, doxophylline, and the like; beta-2-broncodilators, such as salbutamol, fenoterol, clenbuterol, bambuterol, salmeterol, formoterol and the like; and antiasthmatic antiinflammatory agents such as sodium cromoglycate, and the like.

In the embodiment wherein the early morning pathology which is desireously treated is angina, the pharmaceutically active agent of the formulation is an antiangina agent. Specific examples of antiangina agents include but are not limited to isosorbide mononitrate, isosorbide dinitrate, and the like.

In the embodiment wherein the early morning pathology which is desireously treated is arthritis, the pharmaceutically active agent of the formulation is an antiarthritis agent. Specific examples of antiarthritis agents include but are not limited to antiarthritis non-steroidal antiinflammatory agents such as sulfides, mesalamine, salazopyrin, diclofenac, pharmaceutically acceptable salts of diclofenac, nimesulide, ketoprofen, piroxicam, naproxene, ibuprofen and the like.

In the embodiment wherein the early morning pathology which is desireously treated is arrythmia or hypertension, the pharmaceutically active agent of the formulation is an antiarrhythmic or antihypertension agent. Specific examples of antiarrhythmic or antihypertension agents include but are not limited to calcium antagonists, angiotensin-converting enzyme inhibitors, beta-blockers, centrally active alpha-agonists, alpha-1-antagonists, and the like.

In the embodiment wherein the early morning pathology which is desireously treated is myocardial or cerebral infarction, the pharmaceutically active agent of the formulation is an anticoagulant or antiplatelet agent. Specific examples of anticoagulant or antiplatelet agents include but are not limited to warfarin, acetylsalicylic acid, ticlopidine, and the like.

In the embodiment wherein the early morning pathology which is desireously treated is Parkinson's disease or Parkinsonism, the pharmaceutically active agent of the formulation is an antiParkinson's agent. Specific examples of antiParkinson's agents include but are not limited to dopamine, L-Dopa/Carbidopa, selegiline, dihydroergocryptine, bromocriptine, pergolide, lisuride, apomorphine and the like.

In the embodiment wherein the early morning pathology which is desireously treated is sleep disorder such as those associated with anticipated wakening, the pharmaceutically active agent of the formulation is a sedative or ansiolytic agent. Specific examples of sedative or ansiolytic agents include but are not limited to benzodiazepines and the like.

In the embodiment wherein the early morning pathology which is desireously treated is incontinence, the pharmaceutically active agent of the formulation is a anticholinergic or antispasmodic agent or a vasopressin analogue. Specific examples of anticholinergic or antispasmodic agents and vasopressin analogues include but are not limited to flavoxate, oxybutynin, desmopressin, and the like.

Specific examples of suitable peptide or biopolymeric agents include but are not limited to calcitonin, leuprolide and other LHRH agonists, hirudin, cyclosporin, insulin, somatostatin, protirelin, interferon, desmopressin, thymopentin, pidotimod, ematopoietin, melatonin, granulokyne, and heparin.

The core of the time-specific formulation of the present invention may also include one or more pharmaceutically acceptable excipients in addition to the pharmaceutically active agent. Pharmaceutically acceptable excipients which may be employed are well known to those skilled in the art and include any conventional pharmaceutically acceptable tabletting excipients. Examples of suitable excipients include but are not limited to microcrystalline cellulose, dibasic calcium phosphate dihydrate, starch, sodium starch glycolate, crospovidone, croscarmellose sodium, magnesium stearate, lactose, maleic acid, colloidal silicon dioxide, talc, and glyceryl behenate.

In one particularly preferred embodiment, the core of the time-specific formulation includes, in addition to the pharmaceutically acceptable agent, a disintegration enhancing agent. The disintegration enhancing agent accelerates the disintegration of the core once the swellable polymeric coating layer is removed by dissolution or erosion. The disintegration enhancing agent provides the advantage that the pharmaceutically active agent is more readily delivered to the system by virtue of the faster disintegration of the core. The faster delivery of the pharmaceutically active agent to the system which results from the presence of the disintegration enhancing agent within the core advantageously produces a "spike" in the level of pharmaceutically active agent in the system. Thus, in the embodiment wherein the disintegration enhancing agent is present in the core, the pharmaceutically active agent is delivered substantially faster which causes the level of pharmaceutically active agent in the system to rapidly reach the maximum level, rather than more slowly as a stream which gradually reaches the maximum level of delivered drug. Suitable disintegration enhancing agents for use in the methods of the present invention include pharmaceutically acceptable excipients capable of generating effervescence. Specific examples of suitable disintegration enhancing agents include but are not limited to food acids, such as citric acid, tartaric acid, fumaric acid, maleic acid, succinic acid, and the like; acid anhydrides, such as succinic anhydride, fumaric anhydride, and the like; acid salts such as sodium dihydrogen phosphate, disodium dihydrogen pyrophosphate, sodium dihydrogen citrate, disodium hydrogen citrate, and the like; and carbonates such as sodium bicarbonate, sodium carbonate, potassium bicarbonate, potassium carbonate, sodium sesquicarbonate, calcium carbonate, glycine sodium carbonate, L-lysine carbonate, arginine carbonate, and the like.

The core can be prepared by any suitable tabletting technique known to those skilled in the art. For example, the pharmaceutically active ingredient may be admixed with the excipient(s) and, if present, the disintegration enhancing agent, and advantageously formed into a tablet using a conventional tabletting press, or dosed into a capsule.

According to the methods and formulations of the present invention, the preformed core, is substantially surrounded by a swellable polymeric coating layer. The swellable polymeric coating layer typically comprises a hydrophilic gelling polymer or "swellable polymer" which swells on contact with gastro-intestinal juices to form a continuous film surrounding the core. The coating layer must sufficiently protect the integrity of the core for the desired period of time, without regard to the pH of the medium to which it is subjected. Once the desired, pre-delivery time period has elapsed, the core should be capable of relatively quick disintegration so that the pharmaceutically active agent is released as quickly as possible at the predetermined delivery time. Thus, it is desirable that the formulation be capable of the fast, time-specific release of the pharmaceutically active agent. The polymeric coating layer may be comprised of any suitable hydrophilic gelling polymer known to those skilled in the art. For example, suitable hydrophilic gelling polymers include but are not limited to cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, and the like; and mixtures thereof. Currently, the preferred swellable polymeric coating layer comprises hydroxypropylmethylcellulose.

Alternatively, the swellable polymeric coating layer may be comprised of other substances which are capable of becoming freely permeable with exactly defined kinetics following hydration in aqueous fluids. Such substances include polysaccharides, such as gelatin, saccharose, sorbitol, mannaese, and jaluronic acid; polyaminoacids; polyalcohols; polyglycols; and the like In addition to the foregoing, the swellable polymeric coating layer may also include additional excipients such as lubricants, flow promoting agents, plasticizers, antisticking agents, natural and synthetic flavorings and natural and synthetic colorants. Specific examples of additional excipients include polyethylene glycol, polyvinylpyrrolidone, talc, magnesium stearate, glyceryl behenate, stearic acid, and titanium dioxide.

The swellable polymeric coating layer may be applied to the core using conventional film (or spray) coating techniques, double press coating or by the inventors' new method involving the alternate application of binder and powdered polymeric coating particles. In one preferred embodiment, the swellable polymeric coating layer is applied using film coating techniques whereby the hydrophilic gelling polymer is solubilized in an aqueous solution. Typically, the polymer used for film coating exhibits a viscosity ranging from about 3 to 100 mPa.s. at 25° C. in a 2% aqueous solution.

Although some organic solvents may be employed in the film coating application of the swellable polymeric coating layer, the inclusion of organic solvents in the film coating solution utilized in the methods of the present invention is not required.

The solution of hydrophilic gelling polymer can be applied to the core by any means of film coating including but not limited to fluid bed, or pan coating. Preferably, the solution of polymer is sprayed on the core to form the swellable polymeric coating layer.

The polymer is applied on the core (preferably by film-coating) in order to build the desired thickness of the swellable polymeric coating layer. For example, in the embodiment wherein film coating is employed, the core is sprayed with the solution of polymer until the desired thickness of swellable polymeric coating layer is achieved.

In another preferred embodiment, the swellable polymeric coating layer is applied to the core by an alternating two-step application of a binder solution and powdered polymeric coating particles. In the first step, the core is wet with the binder solution which serves to adhere the powdered polymeric coating particles to the core. Suitable binder solutions may include conventional pharmaceutically acceptable binder agents solubilized in a suitable solvent. Specific examples of binder agents include but are not limited to vinyl polymers, such as polyvinylpyrrolidone, polyvinyl alcohol, and the like; cellulosic polymers, such as hydroxypropylmethylcellulose, hydroxyethylcellulose, hydroxypropylcellulose, and the like; acrylic polymers and copolymers such as methacrylic acid copolymers, ethyl acrylate-methylmethacrylate copolymers, and the like; natural or synthetic gums, such as guar gum, arabic gum, xanthan gum, and the like; proteins or carbohydrates, such as gelatin, pectin, and the like; and mixtures thereof. Currently, polyvinylpyrrolidone is the preferred binder agent.

Suitable solvents for solubilizing the binder agents include solvents which are capable of substantially completely solubilizing the specific binder agent(s) selected and which are pharmaceutically and biologically acceptable for ingestion. Suitable solvents will be readily determinable by those skilled in the art. Water is currently the preferred solvent for solubilizing the binder agent, as it is pharmacologically and biologically well suited for ingestion. However, other examples of suitable solvents will be appreciated by those skilled in the art and are contemplated by the methods of the present invention.

The binder solution should be of sufficient viscosity to enable the wetting of the cores by any suitable wetting technique known to those skilled in the art. For example, the cores may be wetted with the binder solution by rotating the cores in a bath containing the binder solution. The cores may be suitably wetted by manual application of the binder solution by ladling the binder solution over the cores as the cores are rotating in a conventional coating pan.

Alternatively, the cores may be wetted by spraying the binder solution on the cores. In one embodiment, the wetting step is advantageously carried out using conventional automated pan coating equipment wherein the cores are sprayed with the binder solution while rotating in the pan.

To provide the coating layer, the wetted cores are coated with dry, powdered polymeric coating particles which adhere to the binder-wetted core due to the presence of the binder on the surface of the core. The polymeric coating particles typically comprise a hydrophilic gelling polymer or "swellable" polymer which swells on contact with gastrointestinal juices to form a continuous film surrounding the core, as described herein above. Currently, the preferred powdered polymeric particles comprise hydroxypropylmethylcellulose.

Hydroxypropylmethylcellulose is a polymer which is available in many forms, including forms of different molecular weight, extremely different viscosity and different substitution grade. The inventors have also discovered that it is advantageous in certain applications to utilize mixtures or blends of two or more different forms of hydroxypropylmethylcellulose as the polymeric coating particles. In one preferred embodiment, the polymeric coating particles of the coating layer comprise a mixture of polymeric coating particles having differing molecular weights and solubility characteristics. For example, the coating layer may be comprised of polymeric coating particles comprising a mixture of a) hydroxypropylmethylcellulose having i) a typical weight percent substitution corresponding to 29% methoxyl and 8% hydroxypropoxyl groups, and ii) a nominal viscosity of a 2% watery solution at 20° C. ranging from 3 to 100 mPa.s; and b) hydroxypropylmethylcellulose having i) a typical weight percent substitution corresponding to 22.1% methoxyl and 8.1% hydroxypropoxyl groups, and ii) a nominal viscosity of a 2% watery solution at 20° C. ranging from 4,000 to 100,000 mPa.s. An example of the first type of hydroxypropylmethylcellulose is METHOCEL E5®, and an example of the second type is METHOCEL K15M®, both of which are commercially available from Colorcon.

The polymer(s) of the swellable polymeric coating layer partially hydrates on the outer surface thereof after ingestion to form a gel-like layer that acts as a skin, controlling the rate of erosion of the coating layer. As a consequence, the release or delivery of the pharmaceutically active agent contained within the core is inhibited for the predetermined period of time.

Grades of hydroxypropylmethylcellulose having different degrees of substitution also possess different rates of hydration. The inventors have discovered that by utilizing mixtures or blends of two or more polymers with different rates of hydration, it is possible to obtain a layer with improved characteristics in terms of the rate-controlled hydration of the same.

Because the formulations and methods of the present invention may include either a single hydroxypropylmethylcellulose or a blend of two or more different forms of hydroxypropylmethylcellulose as the powdered polymeric coating particles, for simplicity, the term "hydroxypropylmethylcellulose" as used herein, including the claims, refers to either a single hydroxypropylmethylcellulose or a blend of two or more forms of the polymer.

After the powdered polymeric coating particles are applied to the wetted core, the steps of first, wetting the core with binder and second, coating with the powdered polymeric coating particles are repeated sequentially one or more additional times in order to build the desired thickness of the swellable polymeric coating layer around the core. In other words, the alternating steps of wetting the core and coating with the powdered polymeric coating particles are repeated in alternate fashion so that prior to each application of the powdered coating particles, the core is first wetted with the binder solution. In this manner, the repeated applications of binder solution and powdered polymeric coating particles build or increase the thickness of the swellable polymeric coating layer to the desired measure. The number of repeated wetting and coating cycles is dependent upon the desired delivery time of the pharmaceutically active agent. The thicker the swellable polymeric coating layer around the core, the longer the latency or lag time prior to delivery of the pharmaceutically active agent.

The swellable layer may also be applied by double-press coating, also known as compression-coating. The main advantage in comparison with the film-coating or the sugar-coating procedure is the elimination of water or other solvents during manufacturing. The manufacturing scheme normally starts with the loading of the bottom layer into the die from the hopper, then the core is centered on the bed of coating, this operation is followed by the deposition of the top layer of the coating. Finally, the whole is compressed by passing the punches between the compression rolls.

Irrespective of the method of application, the swellable polymeric coating layer is typically applied to the core to achieve the desired predetermined thickness of swellable polymeric coating. The desired predetermined thickness of the swellable polymeric coating layer is dependent upon the desired lag time or delay prior to delivery of the pharmaceutically active agent. The thicker the swellable polymeric coating layer around the core, the longer the latency, or lag time prior to delivery of the agent. Typically, the swellable polymeric coating layer is applied to a thickness sufficient to achieve a weight gain of between about 5 and about 500 percent, preferably between about 10 and about 200 percent as determined by solid substance. The swellable polymeric coating layer is sufficiently thick to provide a core:coating layer weight ratio of between about 20:1 and about 1:5 inclusive, or a thickness in excess of about 10 μm up to about 3 mm, inclusive. Preferably, the swellable polymeric coating layer is sufficiently thick to achieve a core:coating layer weight ratio of between about 5:1 and about 1:3 inclusive, or a thickness of between about 50 μm and about 1500 μm.

The methods of the present invention for the treatment of early morning pathologies are particularly advantageous because the time-specific formulation of the present invention permits the delivery of a pharmaceutically active agent at the time that the therapeutic effects of the agent are needed and beneficial while avoiding the constant exposure of the body to drug. Conventionally, early morning pathologies are treated by maintaining constant levels of drug in the body so that the therapeutic effects of the drug are continually present. However, the therapeutic effects of the drug are generally not continuously required throughout the night-time, and thus the maintenance of constant drug levels in the subject causes unnecessary exposure to drug at times when the therapeutic effects of the drug are not required. The methods of the present invention avoid the unnecessary exposure of the body to drug during those times when the therapeutic effects of the drug are not needed (i.e., early during night-time just after the subject falls asleep) while still providing the therapeutic effects of the drug when needed, i.e., during late night-time and at the period of awakening. This advantage is achieved by administering a pharmaceutical formulation according to the present invention prior to sleeping. The pharmaceutical formulation of the present invention delays the release of the pharmaceutically active agent so that the agent is delivered at about the last few hours of night or sleep or at the time of awakening to treat the early morning pathology. Although the formulation has been ingested prior to sleeping, the pharmaceutically active agent is not delivered until about the last few hours or night-time or sleeping or the time of awakening so that the subject is not exposed to the pharmaceutically active agent throughout the entire night.

In one embodiment, the time-specific formulation for use in the methods of the present invention includes multiple time-specific dosage units. The first time-specific dosage unit includes (1) a core comprising the pharmaceutically active agent and a disintegration enhancing agent, and (2) a swellable polymeric coating layer substantially surrounding the core. The second time-specific dosage unit includes (1) a core comprising the pharmaceutically active agent without the disintegration enhancing agent, and (2) a swellable polymeric coating layer substantially surrounding the core. This multi-unit formulation is advantageous in that the presence of the disintegration enhancing agent in the first dosage unit causes the core of that unit of the formulation to more quickly disintegrate and release the pharmaceutically active agent more rapidly, compared to the second unit which does not include the disintegration enhancing unit. The core of the second unit disintegrates and releases the pharmaceutically active agent more slowly and gradually, as compared to the first unit. The disintegration of the first unit provides a quick delivery of the pharmaceutically active agent while the slower disintegration of the second unit provides a continuing delivery stream of pharmaceutically active agent. The result is a single pharmaceutical formulation which provides quick onset of the therapeutic benefits of the pharmaceutically active agent with prolonged effects of those benefits.

Suitable patient populations for which the methods and formulations of the present invention are directed include mammals in general, and in particular, humans.

This invention may be embodied in many different forms and should not be construed as limited to the embodiments set forth herein; rather, these embodiments are provided so that this disclosure will be thorough and complete, and will fully convey the scope of the invention to those skilled in the art. Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. Although specific terms are employed, they are used in a generic and descriptive sense only and not for purposes of limitation, and that modifications and embodiments are intended to be included within the scope of the appended claims.

The following examples are provided to further illustrate specific embodiments of the present invention, and should not be construed as limiting thereof. In these examples, "mg" means milligrams, "g" means grams, "mm" means millimeters, "μm" means micrometer, "kp" means 9.807 Newton, "mPa.s" means milliPascal per second, "min." means minute(s), and "°C." means degrees Centigrade. All percentages are in percent by weight of the tablet unless otherwise indicated. Disintegration tests are carried out according to the standard procedures set forth in the United States Pharmacopoeia for testing the disintegration of tablets.

EXAMPLE 1

Diclofenac sodium (25 mg), 94.5 mg of dibasic calcium phosphate dihydrate, 113 mg of microcrystalline cellulose, 25 mg of tartaric acid, 25 mg of sodium bicarbonate and 1.5 mg of colloidal silicon dioxide, are mixed thoroughly. Magnesium stearate (1 mg) is added and thoroughly mixed for another 5 min. The granular mixture is formed into tablet cores of 8.7 mm diameter, weighing 285 mg each, using a rotary tablet press. The cores show a disintegration time lower than 1 min. in water, a Schleuninger hardness higher than 10 kp, and a friability lower than 0.1%.

The swellable polymeric coating layer is applied on to the tablets in an automatic coating pan using the following solution:

| | |
|---|---|
| Hydroxypropylmethylcellulose (METHOCEL E50 ®) | 7.5% w/w |
| PEG 6000 | 1.5% w/w |
| Purified water | 91.0% w/w |

The solution is applied until a weight gain corresponding to 50% of core weight is achieved. The coated tablets show a dissolution time lag in excess of 300 min., followed by a quick disintegration of the tablet.

EXAMPLE 2

Cores (20,000) containing 25 mg diclofenac sodium are prepared according to Example 1.

The cores are heated to 40° C. and the coating layer is applied onto the cores in a two-step procedure, using an automatic coating pan. In the first step, the cores are wetted with a binder solution including 5% METHOCEL E5®, 10% polyvinylpyrrolidone, and 85% purified water. In the second step, the wetted cores are treated with a dry mixture including 90% METHOCEL K15M®, 9% talc and 1% colloidal silicon dioxide. Steps 1 and 2 are repeated until a weight gain corresponding to 30% of total tablet weight is achieved.

The coated tablets showed a dissolution time lag in excess of 300 min., followed by a quick disintegration of the tablet.

EXAMPLE 3

Verapamil HCl (40 mg), 79 mg of dibasic calcium phosphate dehydrate, 18 mg of microcrystalline cellulose, 25 mg of citric acid, 35 mg of sodium bicarbonate, and 2 mg of colloidal silicon dioxide, are mixed thoroughly. Magnesium stearate (1 mg) is added and thoroughly mixed for another 5 min. The granular mixture is formed into tablet cores of 6.8 mm diameter, weighing 200 mg each using a rotary tablet press. The cores show a disintegration time lower than 1 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 5% METHOCEL E5®, 10% polyvinylpyrrolidone, and 85% purified water. In the second step, the wetted cores are treated with a dry mixture including 90% METHOCEL K15M®, 9% talc and 1% colloidal silicon dioxide. Steps 1 and 2 are repeated until a weight gain corresponding to 50% of total tablet weight is achieved.

The coated tablets showed a dissolution time lag in excess of 300 min., followed by a quick disintegration of the tablet.

EXAMPLE 4

Isosorbide-5-mononitrate (20 mg), 135 mg of Lactose S.D., 34 mg of microcrystalline cellulose, 30 mg of glycine sodium carbonate, 10 mg of fumaric acid, and 5 mg of colloidal silicon dioxide are mixed thoroughly. Magnesium stearate (1 mg) is added and thoroughly mixed for another 5 min. The granular mixture is formed into tablet cores of 8.7 mm diameter, weighing 280 mg each using a rotary tablet press. The cores show a disintegration time lower than 1 min. in water, a Schleuninger hardness higher than 10 kp and a friability lower than 0.1%.

The swellable polymeric coating layer is applied onto the tablets in an automatic coating pan using the following solution:

| Hydroxypropylmethylcellulose (METHOCEL E50 ®) | 8.0% w/w |
| PEG 6000 | 2.0% w/w |
| Purified water | 90.0% w/w |

The solution is applied until a weight gain corresponding to 50% of core weight is achieved. The coated tablets show a dissolution time lag in excess of 300 min., followed by a quick disintegration of the tablet.

EXAMPLE 5

Tablet cores containing 1 mg of lorazepam as the active ingredient, 25 mg of tartaric acid, and 25 mg of sodium bicarbonate as an effervescent disintegration enhancing agent are heated to 40° C. and coated in a two-step procedure, using an automatic coating pan. In the first step, the cores are wetted with a binder solution including 15% polyvinylpyrrolidone and 85% purified water. In the second step, the wetted cores are treated with a dry mixture including 45% METHOCEL E5®, 45% NATROSOL HHR®, 9% talc and 1% colloidal silicon dioxide. Steps 1 and 2 are repeated until a weight gain corresponding to 35% of total tablet weight is achieved. The coating layer is determined to be approximately 0.7–0.8 mm in thickness. The coating time was 6 hours. The coated tablets showed a disintegration time lag in excess of 300 min.

EXAMPLE 6

Comparative Example—Fluid Bed Coating

Tablets containing 1 mg of lorazepam are coated with a coating layer using a fluid bed apparatus. The cores are heated to 40° C. and the coating layer is applied by continuously spraying a solution including 7.5% METHOCEL E50 ®, 0.5% PEG 6000®, 1% colloidal silicon dioxide, and 91% purified water, until a layer corresponding to 50% weight gain is applied. The coated tablets showed a disintegration time lag in excess of 300 min.

EXAMPLE 7

Bromocryptine mesylate (2.87 mg), 30 mg of microcrystalline cellulose, and 20 mg of maleic acid are mixed thoroughly. Lacose S.D. (125.78 mg), 20 mg of sodium carbonate, 0.35 mg colloidal silicon dioxide, and 1 mg magnesium stearate are added and thoroughly mixed for another 10 min. The granular mixture is formed into tablet cores of 6.8 mm diameter, weighing 200 mg using a rotary tablet press. The cores show a disintegration time lower than 1 min. in water, a Schleuringer hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 7% METHOCEL E50®, 3% PEG 400®, and 90% purified water. In the second step, the wetted cores are treated with a dry mixture including 90% METHOCEL K15M®, 9% talc and 1% colloidal silicon dioxide. Steps 1 and 2 are repeated until a weight gain corresponding to 30% of total tablet weight is achieved. The coated tablets showed a disintegration time lag in excess of 5 hours followed by a rapid dissolution profile.

EXAMPLE 8

A capsule (I) containing a total amount of 75 mg of diclofenac sodium is composed of: (II) a tablet containing 25 mg of diclofenac sodium able to promptly release the active after about 5 hours from the ingestion; and (III) two tablets containing each 25 mg of diclofenac sodium able to start a sustained release of the active ingredient after about 5 hours from the ingestion. The system is manufactured as follows:

Tablets (II):

Diclofenac sodium (25 mg), 65 mg of dibasic calcium phosphate dihydrate, 38 mg of microcrystalline cellulose, 25 mg of tartaric acid, 25 mg of sodium bicarbonate and 1 mg of colloidal silicon dioxide, are mixed thoroughly. Magnesium stearate (1 mg) is added and thoroughly mixed for another 5 min. The granular mixture is formed into tablet cores of 6 mm diameter, and about 5.8 mm high, weighing 180 mg each, using a rotary tablet press. The cores show a disintegration time lower than 1 min. in water, a Schleuninger hardness higher than 10 kp and a friability lower than 0.1%. A swellable polymeric coating layer is applied onto the tablets in an automatic coating pan using the following solution:

| Hydroxypropylmethylcellulose (METHOCEL E50 ®) | 7.5% w/w |
| PEG 6000 | 1.5% w/w |
| Purified water | 91.0% w/w |

The solution is applied until a weight gain corresponding to 50% of core weight is achieved. The coated tablets show a dissolution time lag in excess of 240 min., followed by a quick disintegration of the tablet.

Tablets (III):

Diclofenac sodium (25 mg), 85 mg of dibasic calcium phosphate dihydrate, 49 mg of microcrystalline cellulose, 20 mg of hydroxypropylmethylcellulose (METHOCEL K15M®), are mixed thoroughly. Magnesium stearate (1 mg) is added and thoroughly mixed for another 5 min. The granular mixture is formed into tablet cores of 6 mm diameter, and about 5.8 mm high, weighing 180 mg each, using a rotary tablet press. The cores show a dissolution profile of zero order until the 80% of the active is dissolved in more than 8 hours, a Schleuninger hardness higher than 10 kp and a friability lower than 0.1%.

A swellable polymeric coating layer is applied onto the tablets in an automatic coating pan using the same technological approach described for Tablets (II).

The coated tablets show absence of dissolution for at least 240 min., followed by a sustained release of the active for more than 8 hours.

Capsules (I)

One tablet (II), and two tablets (III) are dosed into a capsule size 00, corresponding to a total amount of 75 mg of diclofenac sodium. The capsules show absence of dissolution for about 4 hours, followed by a prompt dissolution of a fraction of 25 mg of the active ingredient and the sustained release of the remaining 50 mg of diclofenac sodium for at least 8 hours.

The foregoing is illustrative of the present invention and is not to be construed as limiting thereof. The invention is defined by the following claims, with equivalents of the claims to be included therein.

That which is claimed:

1. A method for treating an early morning pathology, said method comprising administering to a subject in need of treatment, a time-specific controlled release dosage formulation comprising (1) a core including at least one pharmaceutically active agent effective for the treatment of said morning pathology, and (2) a swellable polymeric coating layer substantially surrounding said core; wherein said formulation is administered prior to sleep, and wherein said swellable polymeric coating layer delays the release of said pharmaceutically active agent from said core for a predetermined period of time dependent upon the thickness of said swellable polymeric coating layer, to permit delivery of said pharmaceutically active agent at about the time of awakening and to treat said early morning pathology.

2. The method according to claim 1, wherein said early morning pathology is asthma and said pharmaceutically active agent is selected from the group consisting of steroids, xanthines, beta-2-agonist bronchodilators, and antiasthmatic non-steroidal antiinflammatory agents.

3. The method according to claim 2, wherein said pharmaceutically active agent is selected from the group consisting of betamethasone, dexamethasone, methylprednisolone, prednisolone, prednisone, triamcinolone, theophylline, aminophylline, doxophylline, salbutamol, fenoterol, clenbuterol, bambuterol, and sodium cromoglycate.

4. The method according to claim 1, wherein said early morning pathology is angina and said pharmaceutically active agent is selected from the group consisting of antiangina agents.

5. The method according to claim 4, wherein said pharmaceutically active agent is selected from the group consisting of isosorbide mononitrate, and isosorbide dinitrate.

6. The method according to claim 1, wherein said early morning pathology is arthritis and said pharmaceutically active agent is an antiarthritis non-steroidal antiinflammatory agents.

7. The method according to claim 6, wherein said pharmaceutically active agent is selected from the group consisting of sulfides, mesalamine, salazopyrin, diclofenac, pharmaceutically acceptable salts of diclofenac, nimesulide, ketoprofen, and piroxicam.

8. The method according to claim 1, wherein said early morning pathology is hypertension and said pharmaceutically active agent is selected from the group consisting of calcium antagonists, angiotensin-converting enzyme inhibitors, beta-blockers, centrally active alpha-agonists, and alpha-1-antagonists.

9. The method according to claim 1, wherein said early morning pathology is myocardial or cerebral infarction and said pharmaceutically active agent is selected from the group consisting of anticoagulant agents and antiplatelet agents.

10. The method according to claim 9, wherein said pharmaceutically active agent is selected from the group consisting of warfarin, acetylsalicylic acid, and ticlopidine.

11. The method according to claim 1, wherein said early morning pathology is Parkinson's disease or Parkinsonism and said pharmaceutically active agent is selected from the group consisting of dopamine, L-Dopa/Carbidopa, selegiline, dihydroergocryptine, and bromocriptine.

12. The method according to claim 1, wherein said early morning pathology is sleep disorder, and said pharmaceutically active agent is selected from the group consisting of sedatives and ansiolytic agents.

13. The method according to claim 12, wherein said pharmaceutically active agent is a benzodiazepine.

14. The method according to claim 1, wherein said early morning pathology is incontinence, and said pharmaceutically active agent is selected from the group consisting of anticholinergic/antispasmodic agents and vasopressin analogues.

15. The method according to claim 14, wherein said pharmaceutically active agent is selected from the group consisting of flavoxate, oxybutynin, and desmopressine.

16. The method according to claim 1, wherein said formulation is administered orally prior to sleep.

17. The method according to claim 1, wherein said swellable polymeric coating layer comprises a hydrophilic swellable polymer selected from the group consisting of methylcellulose, carboxymethylcellulose, hydroxypropylcellulose, hydroxypropylmethylcellulose, hydroxyethylcellulose, polyvinyolpyrrolidone, polyvinyl alcohol, acrylic acid polymer, methacrylic acid copolymers, ethyl acrylate-methyl methacrylate copolymers, natural rubbers, poloxamers, polysaccharides, and mixtures thereof.

18. The method according to claim 1, wherein said swellable polymeric coating layer is applied to said core by film coating.

19. The method according to claim 1, wherein said swellable polymeric coating layer is applied to said core by alternately (i) wetting said core with a binder solution and (ii) coating said core with powdered polymeric coating particles, a sufficient number of times to produce the desired thickness of swellable polymeric coating layer.

20. The method according to claim 19, wherein said binder solution is selected from the group consisting of polyvinylpyrrolidone, hydroxypropylmethylcellulose, polyvinyl alcohol, hydroxyethylcellulose, hydroxypropylcellulose, methylcellulose, methacrylic acid copolymers, ethyacrylate-methylmethacrylate copolymers, guar gum, arabic gum, xanthan gum, gelatine, pectin and mixtures thereof; and said powdered polymeric coating particles comprise a hydrophilic swellable polymer selected from the group consisting of methylcellulose, carboxymethylcellulose, hydroxypropylcellulose, hydroxypropylmethylcellulose, hydroxyethylcellulose, polyvinyolpyrrolidone, polyvinyl alcohol, acrylic acid polymer, methacrylic acid copolymers, ethyl acrylate-methyl methacrylate copolymers, natural rubbers, poloxamers, polysaccharides, and mixtures thereof.

21. The method according to claim 1, wherein said swellable polymeric coating layer comprises hydroxypropylmethylcellulose.

22. The method according to claim 1, wherein said swellable polymeric coating layer comprises a mixture of 1) hydroxypropylmethylcellose having a typical weight percent substitution corresponding to 29% methoxyl and 8% hydroxypropoxyl groups, and a nominal viscosity of 2% water solution at 20° C. ranging from 3 to 100 mPa.s; and 2) hydroxypropylmethylcellulose having a typical weight percent substitution corresponding to 22.1% methoxyl and 8.1% hydroxypropoxyl groups, and a nominal viscosity of 2% water solution at 20° C. ranging from 4,000 to 100,000 mPa.s.

23. The method according to claim 1, wherein said swellable polymeric coating layer is sufficiently thick to achieve a core:coating layer weight ratio of between about 20:1 and about 1:5.

24. The method according to claim 1, wherein said swellable polymeric coating layer is sufficiently thick to achieve a core:coating layer weight ratio of between about 5:1 and about 1:3.

25. The method according to claim 1, wherein said swellable polymeric coating layer is not less than about 50 µm thick.

26. The method according to claim 1, wherein said core further comprises a disintegration enhancing agent.

27. The method according to claim 26, wherein said disintegration enhancing agent is selected from the group consisting of citric acid, tartaric acid, fumaric acid, maleic acid, succinic acid, succinic anhydride, maleic anhydride, sodium dihydrogen phosphate, disodium dihydrogen pyrophosphate, sodium dihydrogen citrate, disodium hydrogen citrate, sodium bicarbonate, sodium carbonate, potassium bicarbonate, potassium carbonate, sodium sesquicarbonate, glycine sodium carbonate, calcium carbonate, L-lysine carbonate, and arginine carbonate.

* * * * *